United States Patent [19]
Martin et al.

[11] Patent Number: 4,904,674
[45] Date of Patent: Feb. 27, 1990

[54] 1-(BENZO[B]THIENYL)-2-(THIENYL)ETHENES AND RELATED COMPOUNDS USEFUL AS ANTI-INFLAMMATORY AGENTS

[75] Inventors: Lawrence L. Martin, Lebanon; Joseph F. Payack, Somerset, both of N.J.

[73] Assignee: Hoechst-Roussel Pharmaceuticals Inc., Somerville, N.J.

[21] Appl. No.: 394,690

[22] Filed: Aug. 16, 1989

[51] Int. Cl.$^4$ .................. C07D 409/14; A61K 31/38; A61K 31/44
[52] U.S. Cl. .................................. 514/337; 514/444; 546/274; 549/51; 549/58
[58] Field of Search .................... 546/274; 549/49, 51, 549/58; 514/337, 444

[56] References Cited

FOREIGN PATENT DOCUMENTS 0181568 1/1986 European Pat. Off. .

OTHER PUBLICATIONS

Y. Tominaga et al., J. Heterocyclic Chem. 18, 967 (1981).
Y. Tominaga et al., J. Heterocyclic Chem. 19, 871 (1982).
H. Kudo et al., J. Heterocyclic Chem., 21, 185 (1984).

Primary Examiner—Richard A. Schwartz
Assistant Examiner—Richard A. Sharpe
Attorney, Agent, or Firm—Raymond R. Wittekind

[57] ABSTRACT

Novel 1-(benzo[b]thienyl)-2-(thienyl)ethenes, processes for the preparation thereof, and methods of reducing inflammation utilizing compounds and compositions there are disclosed.

28 Claims, No Drawings

1-(BENZO[B]THIENYL)-2-(THIENYL)ETHENES AND RELATED COMPOUNDS USEFUL AS ANTI-INFLAMMATORY AGENTS

The present invention relates to 1-(benzo[b]thienyl)-2-(thienyl)ethenes. More particularly, the present invention relates 1-(benzo[b]thienyl)-2-(thienyl)ethenes of formula 1

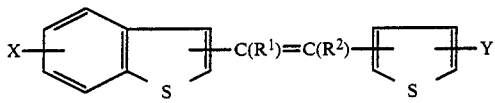

wherein $R^1$ and $R^2$ are independently hydrogen or alkyl; X is hydrogen, alkyl, alkoxy, halogen, or trifluoromethyl; Y is halogen, alkyl, hydroxymethyl, formyl, carboxy, alkoxycarbonyl, alkanoyloxymethyl, (N-alkyl-N-hydroxyamino)carbonyl, (N-cycloalkyl-N-hydroxyamino)carbonyl,(N-cycloalkyl-N-hydroxyamino)alkyl, ω-haloalkyl, carboxyalkylidene, alkoxycarbonylalkylidene, (N-alkyl-N-hydroxyamino)alkyl, a group of the formula

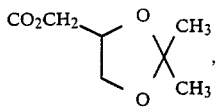

a group of the formula

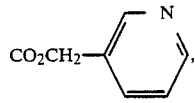

a group of the formula $CO_2CH_2CH(OH)CH_2OH$, a group of the formula $CH(OH)CH(CO_2R^3)NHCOR^4$ wherein $R^3$ and $R^4$ are alkyl, a group of the formula $CH(OH)CH(CH_2OH)NHCOR^4$ wherein $R^4$ is alkyl, or a group of the formula $CH(OH)CH(CH_2OH)NH_2$; the geometric and optical isomers thereof, or the pharmaceutically acceptable salts thereof, which are useful for the reduction of inflammation, alone or in combination with inert adjuvants.

1-(Benzo[b]thienyl)-2-(thienyl)ethenes wherein $R^1$ and $R^2$ are hydrogen; X is hydrogen; and Y is hydroxymethyl, carboxylakylidene, or (N-alkyl-N-hydroxyamino)carbonyl are preferred.

As used through the specification and appended claims, the terms "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 3-hexyl, 4-heptyl, 2-octyl, 3-nonyl, 4-decyl and the like; the term "cycloalkyl" refers to a saturated hydrocarbon group possessing at least one carbocyclic ring of from 3 to 8 carbon atoms such as cyclopropyl, cyclobutyl, cyclopentyl, cyclohexyl, cycloheptyl, cyclooctyl and the like; the term "alkylidene" refers to a straight or branched chain hydrocarbon radical containing unsaturation in the form of a single carbon to carbon double bond and having from 3 to 10 carbon atoms such as propenyl, 2-butenyl, 2-methyl-2-butenyl, 3-hexenyl, 3-ethyl-2-pentenyl, 3-methyl-3-heptenyl, nonenyl, decenyl, and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, 2-methyloctoxy, octoxy, decoxy, and the like; the term "alkanol" refers to a compound formed by a combination of an alkyl group and hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "halogen" refers to a member of the family fluorine, chlorine, bromine, or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, decanoyl and the like. The term "lower" as applied to any of the aforementioned groups refers to a group having a carbon skeleton containing up to and including 8 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, those instant compounds characterized by the presence of an acidic carboxylic acid group and an optically active base, or by the synthesis from optically active precursors.

The present invention comprehends all optical isomers and racemic forms thereof and all geometric isomers of the compounds disclosed and claimed herein. The formulas of the compounds shown herein are intended to encompass off possible geometric and optical isomers of the compounds so depicted.

The novel 1-(benzo[b]thienyl)-2-thienyl)ethenes of the present invention are synthesized by the processes illustrated in Reaction Schemes A to F.

To synthesize 1-(benzo[b]thienyl)-2-(thienyl)ethenes in which the ethenyl group links the 2-positions of the heterocycles, i.e., to gain entry into the 2,2-series as typified by ethenes of formulas 3 to 9, a phosphonate of formula 2, the preparation of which is described in Y. Tominaga, et al., Journal of Heterocyclic Chemistry, 19, 871 (1982), is condensed with a thiophene of formula 10.

wherein $R^2$ is as previously described and Hal is fluoro, chloro, bromo, or iodo to afford ethene 3. A halothienylethene 3, so obtained, is subsequently converted to a carboxythienylethene 3, which is transformed to an alkoxycarbonylthienyl- of formula 5, or an N-alkyl-N-hydroxyaminocarbonylthienylethene or an N-cycloalkyl-N-hydroxyaminocarbonylthienylethene of formula 6. See Reaction Scheme A.

The condensation is performed by contacting a phosphonate 2 with an aldehydo or ketothiophene 10 in the presence of a base and a suitable solvent. Among bases there may be mentioned hydrides such as lithium hydride, sodium hydride, or potassium hydride, sodium hydride being preferred. Among suitable solvents there may be mentioned ethereal solvents such as dimethoxyethane, 2-methoxyethyl ether, dioxane, and tetrahydrofuran, dimethoxyethane being preferred. The condensation temperature is not narrowly critical. It is preferred, however, to carry out the reaction at ambient temperature.

The conversion of a halothienylethene 3 to a carboxythienylethene 4 is accomplished by metalation of 3 in an ethereal solvent such as, for example, tetrahydrofuran or dimethoxyethane with an alkyl- or aryllithium such as, for example, n-butyllithium or phenyllithium, followed by carboxylation of the intermediate thienyllithium, so obtained, with carbon dioxide, preferably in the form of dry ice. n-Butyllithium and tetrahydrofuran are the preferred metalating agent and reaction solvent. The metalation and carboxylation reactions are performed at a temperature within the range of about −100° to about −40° C., preferably at a temperature of about −70° C.

The transformations of carboxythienylethene 4 to the corresponding esters and hydroxamic acids, 5 and 6, respectively, are accomplished by converting the acid 3 to its acid halide by means of, for example, a thionyl halide, phosphorous trihalide, phosphorous pentahalide, or phosphorous oxyhalide, in a haloalkane, for example, dichloromethane or trichloromethane, an ethereal solvent, for example, diethyl ether, 1,2-dimethoxyethane, tetrahydrofuran, dioxane, or 2-methoxyethyl ether, or an aromatic hydrocarbon, for example, benzene, toluene, xylene, or mesitylene, and, without purification, treating the intermediate acid halide with an alkanol of formula 11

$$R^5OH \qquad 11$$

wherein $R^5$ is alkyl or cycloalkyl in the presence of an acid acceptor such as pyridine or triethylamine, pyridine being preferred, or a hydroxylamine of formula 12

$$R^6NHOH \qquad 12$$

wherein $R^6$ is alkyl or cycloalkyl in a halocarbon solvent also in the presence of an acid acceptor, for example, pyridine or triethylamine, triethylamine being preferred. The preferred acid halide is a thionyl halide; most preferred is thionyl chloride. The preferred solvent for the halogenation and hydroxyamination steps is a haloalkane; most preferred is dichloromethane. The esterification and hydroxamination proceed readily at the reflux temperature of the reaction mixture. Reduced temperatures within the range of from about ambient temperature to about the reflux temperature may be employed, however.

Additional members of the 2,2-series of ethenes characterized by the presence of a haloalkylthienyl, an N-alkyl-N-hydroxyaminoalkylthienyl or an N-cycloalkyl-N-hydroxyaminoalkylthienyl moiety are prepared by the haloalkylation of a 1-(benzo[b]thienyl-2-(thienyl)ethene of formula 7, the synthesis of which is reported in H. Kudo, et al., Journal of Heterocyclic Chemistry, 21, 185 (1984), to provide a haloalkylthienylethene 8 which is transformed to a hydroxyaminoalkylthienylethene or hydroxyaminocycloalkylthienylethene 9. See Reaction Scheme B.

The haloalkylation is accomplished by treatment of a thiophene 7 with an aryllithium (e.g., phenyllithium) in an ethereal solvent (e.g., tetrahydrofuran) as hereinbeforedescribed for the metalation of halothienylethene 3 to yield lithiothiophene intermediate which, without isolation is contacted with an α-107-dihaloalkane of formula 13

$$Hal(CH_2)_nHal \qquad 13$$

wherein Hal is as described hereinbefore and n is 1 to 6 in the presence or absence of an ethereal solvent to give haloalkylthiophene 8.

The hydroxamination of 8 to 9 is conducted by treating a haloalkylthiophene 8 with a salt of an N-hydroxy-N-alkylamine or N-hydroxy-N-cycloalkylamine of formula 12 in the presence of a base and an ethereal solvent. Included among salts of hydroxylamine 12 are the hydrochloride, hydrobromide, and sulfate. Included among bases are alkali metal alkoxides such as lithium methoxide, sodium methoxide, potassium methoxide and the corresponding ethoxides, 2-propoxides, and t-butoxides. Included among ethereal solvents are dimethoxyethane, 2-methoxyethylether, dioxane, and tetrahydrofuran. The hydrochloride, potassium t-butoxide, and tetrahydrofuran are the preferred salt, base, and ethereal solvent, respectively. The hydroxamination temperature is not critical. An elevated temperature of about the reflux temperature of the reaction medium is usually employed to assure a reasonable rate of conversion.

To elaborate the 3,2-series, i.e., to synthesize 1-(benzo[b]thienyl)-2-(thienyl)ethenes in which the ethenyl group bridges the 3-position of the benzothiophene moiety with the 2-position of the thiophene system, a phosphonate 14, the preparation of which is described in Y. Tominaga, et al., Journal of Heterocyclic Chemistry, 18, 969 (1981), is condensed with a thiophene of formula 10 to yield ethene 15 wherein $R^1$, $R^2$, X, and Hal are as hereinbeforedescribed. A halothienyethene 15 is obtained, is subsequently converted to a carboxythienylethene 16, which is then esterified to 17 wherein $R^8$ is alkyl, a group of the formula

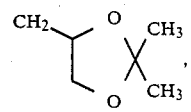

or a group of the formula

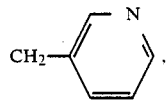

and hydroxaminated to 18 wherein $R^6$ is alkyl. See Reaction Scheme C.

The condensation of a phosphonate 14 with an aldehydo- or alkanoylthiophene 10 is accomplished by the process for the conversion of phosphonate 2 to halothiophene 3 as described above. Likewise, the carboxylation of halothiophene 15 to carboxythiophene 16 is effected by the process for the conversion of halothiophene 3 to carboxythiophene 4, with the exception that diethylether is the preferred solvent.

The esterification of carboxythiophene 16 is conducted by the processes hereinbeforedescribed for the conversion of carboxythiophene 4 to the corresponding ester 5 utilizing an alkanol of formula 19

$$R^8OH \qquad 19$$

wherein $R^8$ is as above.

A thiophenecarboxylic acid 2,3-dihydroxypropyl ester of formula 17 wherein $R^8$ is a group of the formula $CH_2CH(OH)CH_2OH$ is prepared by cleavage of a thiophenecarboxylic acid dioxolanylhydroxy ester 17 wherein $R^8$ is a group of the formula

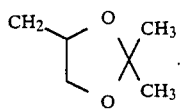

The cleavage is performed under conditions so that the carboxylic acid ester group is not disturbed. For example, treatment of dioxolanylhydroxy ester 17 with boric acid in the presence of a trialkylborate, such as triethylborate, at a reaction temperature of about 80° to about 120° C., a cleavage temperature of about 100° C. being preferred, provides the desired dihydroxypropyester 17.

The hydroxyamination of thiophene carboxylic acid 16 is achieved by the process described above for the conversion of carboxythiophene 4 to thiophenecarbamic acid 6.

To introduce an alkyl group into the thienyl function of a thienylethenylbenzo[b]thiophene, i.e., to synthesize an alkylthiophene of formula 19 wherein $R^{11}$ is alkyl, a halothiophene 15 is lithiated with an alkyl- or aryllithium e.g. n-butyllithium or phenyllithium, in an ethereal solvent, e.g., diethyl ether, dimethoxyethane, or tetrahydrofuran, at a reduced temperature, to form a lithio derivative which, without isolation, is alkylated with an alkyl halide of formula 22

$$R^{11}Hal \qquad 22$$

wherein $R^{11}$ is alkyl and Hal is iodo or bromo. The lithiation is preferably performed with an alkyllithium, most preferably with n-butyllithium, in diethyl ether at a temperature within the range of about −100° to about −50° C., most preferably at about −70° C. The alkylation is preferably conducted with an alkyl iodide i.e., an iodide of formula 22 wherein Hal is iodo, at about 25° C.

To furnish a [(hydroxymethylthienyl)ethenyl]benzo[b]thiophene of formula 21 wherein $R^{12}$ is hydrogen, a [(halothienyl)ethenyl]benzo[b]thiophene of formula 15 is converted to an [(aldehydothienyl)ethenyl]benzo[b]thiophene of formula 20 which is reduced to carbinol 21. The conversion of halothiophene 15 aldehydothiophene 20 is effected by metalation of 15 with an alkyl- or aryllithium as hereinbeforedescribed followed by treatment of the lithio intermediate with a N,N-dialkylformamide of formula 23

wherein $R^{13}$ is alkyl in an ethereal solvent, e.g., diethyl ether, dimethoxyethane or tetrahydrofuran, diethyl ether being preferred, at a reaction temperature initially within the range of about −100° to about −50° C., and finally within the range of about 0° to about 50° C., preferably at about −70° and about 25° C., respectively.

The reduction is conveniently conducted by contacting an aldehydothiophene 20 with an alkali metal borohydride or an alkali metal aluminum hydride in an alkanol, or ethereal solvent, respectively. Included among alkali metal borohydrides are lithium borohydride, potassium borohydride, and sodium borohydride. Included among alkali metal aluminum hydrides are lithium aluminum hydride and sodium aluminum hydride. Included among alkanols are methanol, ethanol, 2-propanol, and t-butanol. Included among ethereal solvents are 1,1-dimethoxyethane, tetrahydrofuran, dioxane, or 2-methoxyethyl ether. An alkali metal borohydride and an alkanol are preferred. Sodium borohydride and ethanol are the most preferred reducing agent and solvent. The reduction temperature is not critical. The reduction proceeds at a reasonable rate at a temperature within the range from about 0° to about 50° C., a temperature of about 25° C. being preferred.

A [hydroxymethylthienyl]benzo[b]thiophene 21 ($R^{12}$ is hydrogen) is acylated to an [alkanoyloxymethylthienyl)ethenyl]benzo[b]thiophene 21 ($R^{12}$ is alkanoyl) by conventional methods. For example, treatment of hydroxymethylthiophene 21 ($R^{12}$ is hydrogen) with an alkanoyl halide of formula 24

wherein Hal is chloro or bromo in the presence of a solvent/acid acceptor such as pyridine at about 25° C. provides the acyl derivative 21 ($R^{12}$ is alkanoyl). See Reaction Scheme D.

To introduce a carboxyalkylidene group into the thiophene system of a benzothienylethenylthiophene of the 3,2-series, for example, to prepare a carboxyalkylidenethiophene of formula 25, an aldehydothiophene 20 is condensed with a phosphonate of formula 28

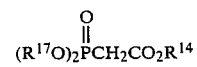

wherein $R^{14}$ and $R^{17}$ are alkyl to afford an alkoxycarbonylalkylidenethiophene of formula 25 wherein $R^1$, $R^2$, $R^{14}$, and X are as above, which is hydrolyzed to the corresponding carboxyalkylidenethiophene of formula 25 wherein $R^{14}$ is hydrogen. The condensation of an aldehyde 20 with a phosphonate 28 is achieved in an ethereal solvent such as, for example, diethyl ether, tetrahydrofuran, or dimethoxyethane, dimethoxyethane being preferred, in the presence of a base, such as sodium hexamethydisilazane or potassium hexamethyldisilazane, potassium hexamethyldisilazane being preferred, at a temperature of about 0° to about 50° C., 25° C. being preferred. See Reaction Schedule E.

The hydrolysis is carried out under standard reaction conditions, namely, an alkali metal hydroxide, e.g., sodium hydroxide or potassium hydroxide, in aqueous tetrahydrofuran, at the reflux temperature of the reaction mixture. Potassium hydroxide is the preferred base.

To prepare a benzo[b]thienylethenylthiophene having a group of the formula CH(OH)CH(NH$_2$)CH$_2$OH bound to the thienyl function, i.e., to synthesize a dihydroxyaminopropylthiophene of formula 27 wherein R$^{15}$ is hydrogen, an aldehydothiophene 20 is condensed with an acylaminomalonate of formula 29

wherein R$^{15}$ is alkanoyl and R$^{16}$ is alkyl to form a thienylacylaminohydroxyproprionate 26 wherein R$^{15}$ and R$^{16}$ are as above which is reduced to a thienylacylaminohydroxy propanol 27 wherein R$^{15}$ is alkanoyl and hydrolyzed to a desired dihydroxyaminopropylthiophene 27 wherein R$^{15}$ is hydrogen. See Reaction Scheme E.

The condensation of aldehyde 20 with malonate 29 is performed in an ethereal solvent, e.g., dimethoxyethane, dioxane or tetrahydrofuran, in the presence of a basic catalyst such as a trialkylamine, e.g., trimethyamine, triethylamine, or tripropylamine, or a heterocyclic amine, e.g., pyridine, picoline, lutididine, or collidine at a temperature within the range of about 20° to about 70° C., a condensation temperature of about 25° C. being preferred. Tetrahydrofuran and triethylamine are the preferred solvent and basic catalyst, respectively.

The reduction of thienylpropionate 26 wherein R$^{15}$ is alkanoyl and R$^{16}$ is alkyl is effected by means of an alkali metal hydride such as lithium borohydride in an ethereal solvent such as dimethoxyethane, tetrahydrofuran, dioxane, preferably at a reaction temperature of about 25° C., although the reduction proceeds readily at a temperature within the range of about 15° to about 50° C. The preferred solvent is tetrahydrofuran.

The hydrolysis of a thienylacylaminohydroxypropanol 27 wherein R$^{15}$ is alkanoyl to a thienylaminohydroxypropanol wherein R$^{15}$ is hydrogen is performed by conventional methods. For example, treatment of an acylamino compound 27 (R$^{15}$ is alkanoyl) with potassium hydroxide in 2-propanol at the reflux temperature of the reaction medium provides the aminodiol 27 wherein R$^{15}$ is hydrogen.

To elaborate a benzo[b]thienylethenylthiophene of the 3,3-series, i.e., to prepare a benzo[b]thienylethenylthiophene of formula 33 wherein R$^1$, R$^2$, and X are as above, a bromothiophene of formula 30 is metalated and the resulting lithiothiophene is condensed with a N,N-dialkylformamide 23 as hereinbefore described to afford aldehydothiophene 31 which is contacted with a 3-benzo[b]thienylphosphonate of formula 32

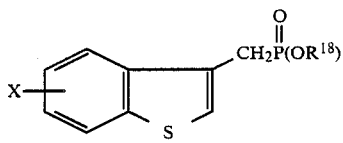

where R$^{18}$ is alkyl and X is as above to provide a hydroxymethylthiophene 33. A hydroxymethylthiophene 33 wherein R$^1$, R$^2$, and X are as above may be converted to derivatives thereof by following the procedures described before for the corresponding conversions in the 2,2- and 3,2-series. See Reaction Scheme F.

The benzo[b]thienylethenylthiophenes of the present invention are useful as antiinflammatory agents due to their ability to reduce inflammation in mammals. The antiinflammatory activity is demonstrated in the TPA-induced ear edema assay and the arachidonic acid-induced ear edema test (see J. M. Young et al., Journal Investigative Dermatology, 80, 48 (1983)).

In the TPA-induced ear edema assay, TPA (12-O-tetradecanoylphorbol-13-acetate) is dissolved in 30/70 propylene glycol/ethanol and is applied to the right ear of groups of 6 female Swiss Webster mice, which were housed together in a cage under standard conditions for 1 week prior to use with food and water ad lib, at a volume of 20 μl so that a total of 10 μg of TPA is delivered to the inner and outer surfaces of the ear. The test compound is dissolved in the vehicle and is applied to the right ear (the inner and outer surface) at a volume of 20 82 1 so that a total of 10 μg of the compound is delivered to the ear. After about 5 hours, the animals are sacrificed, a 4 mm diameter plug is taken from each ear and weighed. The difference between the right and left ear weights for each animal was determined. The antiinflammatory activity of the test compound is expressed as the mean percent change in the ear plug weight of the treated animals compared to the mean percent change in the plug weight of the control animals. Antiinflammatory activity of representative compounds of the instant invention as determined in this assay are presented below in Table 1.

TABLE 1

| Compound | Antiinflammatory Activity Percent Decrease in Ear Plug Weight at 10 μg/ear |
|---|---|
| 5-[2-(benzo[b]thiophen-3-yl)ethenyl]thiophene-2-carboxylic acid | 49 |
| 3-[2-(5-hydroxymethyl-2-thienyl)ethenyl[benzo[b]thiopene | 48 |
| 3-[5-[2-(benzo[b]thiophen-3-yl)ethenyl]thiophen-2-yl]-2-propenoic acid ethyl ester | 58 |
| 5-[2-(benzo[b]thiophen-3-yl)-ethenyl]thiophene-2-(N—methyl)-hydroxamic acid | 56 |
| 3-[2-(2-hydroxymethyl-3-thienyl)ethenyl]benzo[b]thiophene | 60 |
| 3-[5-[2-(benzo[b]thiophen-3-yl)ethenyl]thiophen-2-yl]-2-propenoic acid | 54 |
| Indomethacin | 86 |

In the arachidonic acid-induced ear edema assay, the test compound is dissolved in 30/70 propylene glycol/ethanol and is applied to both ears of groups of 6 female Swiss Webster mice, which were housed together in a cage under standard conditions for 1 week prior to use with food and water ad lib, at a volume of 20 μl so that a total of 1.0 mg of test compound is delivered to each ear over the inner and outer surfaces. The same volume (20 μl) of vehicle is applied to each ear of a control group of mice. After 30 minutes, arachidonic acid is applied to the right ear of each mouse of each group in the amount of 4 mg/ear. Vehicle is applied to the left ear of each mouse of each group at a volume of 20 μl/ear. After an additional hour, the mice are sacrificed and a 4 mm plug is taken from each ear and weighed. The difference between the right and left ear plugs was determined for each animal. The antiinflammatory activity of the test compound is expressed as the mean percent change in the ear plug weight of the treated animals relative to the mean percent change in weights of control animal's ear. Antiinflammatory activity of representative compounds of the present invention as determined in this assay are presented below in Table 2.

TABLE 2

| Compound | Antiinflammatory Activity Percent Decrease in Ear Plug Weight at 1 mg/ear |
|---|---|
| 3-[2-(5-hydroxymethyl-2-thienyl)ethenyl]benzo[b]thiopene | 52 |
| 5-[2-benzo[b]thiophen-3-yl)ethenyl]thiophene-2-carboxylic acid octyl ester | 52 |
| 5-[2-(benzo[b]thiophen-3-yl)-ethenyl]thiophene-2-(N—methyl)-hydroxamic acid | 45 |
| Indomethacin | 90 |

Inflammation reduction is achieved when the present benzo[b]thienylethenylthiophenes are administered topically, including ophthalmic administration, to a subject requiring such treatment as an effective topical dose of from 0.001 to 100 mg/kg of body weight per day. A particularly effective amount is about 25 mg/kg of body weight per day. It is to be understood however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Compounds of the present invention include:
(a) 5-[2-(5-bromobenzo[b]thiophen-2-yl)ethenyl]-thiophene-2-carboxylic acid;
(b) 5-[2-(6-methylbenzo[b]thiophen-2-yl)ethenyl]-thiophene-2-(N-ethyl)hydroxamic acid;
(c) 5-[2-(7-methoxybenzo[b]thiophen-2-yl)ethenyl-2-[3-(N-hydroxy-N-methylamino)propyl]thiophene;
(d) 5-[2-(5-trifluoromethylbenzo[b]thiophen-3-yl)-ethenyl-2-(hydroxmethyl)thiophene;
(e) 5-[2-(benzo[b]thiophen-3-yl)ethenyl]thiophene-2-(N-cyclohexyl)hydroxamic acid; and
(f) 5-[2-(benzo[b]thiophen-3-yl)ethenyl-2-[2-(N-cyclohexyl-N-hydroxyamino)ethyl]thiophene.

Effective amounts of the compounds of the present invention may be administered topically to a subject in the form of sterile solutions, suspensions, ointments, creams, aerosols, or salves. The benzo[b]thienylethenylthiophenes of the present invention, while effective themselves, may be formulated and administered in the form of their pharmaceutically acceptable acid or base addition salts for purposes of stability, convenience or crystallization, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like. Preferred pharmaceutically acceptable base addition salts include salts of alkali metals, e.g. sodium or potassium, alkaline earth metals, e.g. calcium or magnesium; or complex salts such as ammonium or substituted ammonium salts such as a mono-, di- or trialkylammonium salts or a mono, di- or trihydroxyalkylammonium salts.

For the purpose of topical administration, the active compounds of the invention may be incorporated into a solution, suspension, ointment, cream, gel, aerosol, or salve. These preparations should contain at least 0.1% of active compound but may be varied to be between 0.05 and about 20% of the weight thereof. The amount of active compound in such compositions is such that a suitable dosage will be obtained. Preferred topically administered preparations should contain between 0.1 and 10% of active compound.

The topical compositions may also include the following components: water, fixed oils, polyethylene, glycols, glycerol, petroleum, stearic acid, beeswax, other synthetic solvents or mixtures thereof; antibacterial agents such as benzyl alcohol or methyl paraben; antioxidants such as $\alpha$-tocopheral acetate; chelating agents such as ethylenediaminetetraacetic acid; buffers such as acetates, citrates or phosphates; emulsifying agents such as polyoxyethylene monooleate and coloring materials and adjuvants such as ferric oxide or talc. The topical preparation can be enclosed in tubes, bottles, or jars made of metal, glass or plastic.

The following Examples are for illustrative purposes only and are not to be construed as limiting the invention.

EXAMPLE 1

2-[2-(5-Bromo-2-thienyl)ethenyl]benzo[b]thiophene

To a stirred, chilled (2° C.) suspension of hexane-washed sodium hydride (60% dispersion in mineral oil, 5.07 g) and dimethoxyethane (400 ml) was added a solution of 2-benzo[b]thienylphosphonate (30.0 g) and dimethoxyethane (60 ml) over 15 mins. The mixture was stirred 0.5 hr, and then a solution of 5-bromo-2-thiophenecarboxaldehyde (20.25 g), and dimethoxyethane (60 ml) was added over 5 min. The suspension was stirred at room temperature overnight. Water (1 L) was added, and the organic phase was removed in vacuo. The aqueous phase was extracted with dichloromethane, and the combined organic phase was dried over anhydrous sodium sulfate and concentrated. The residue was recrystallized from dichloromethane to give 19.0 g (56%) of product, mp 171°–172° C.

Analysis: Calculated for $C_{14}H_9BrS_2$: 52.34%C; 2.82%H, Found: 52.45%C; 2.73%H.

EXAMPLE 2

5-[2-(Benzo[b]thiophen-2-yl)ethenyl]thiophene-2-carboxylic acid

To a stirred, chilled (−70° C.) suspension of 2-[2-(5-bromo-2-thienyl)ethenyl]benzo[b]thiophene (15.6 g) and tetrahydrofuran (400 ml) was added n-butyl lithium (21.4 ml of a 2.5M solution in hexanes), under nitrogen over 10 mins. The solution was stirred at −70° C. for 1.5 hr, and was transferred via canula to a flask containing a suspension of dry ice (excess) and tetrahydrofuran (1000 ml). The suspension was stirred for 2 hrs and allowed to warm to room temperature overnight. The mixture was poured into water (500 ml), acidified with hydrochloric acid, and the tetrahydrofuran was removed in vacuo. The resulting suspension was filtered, and the filter cake was washed with water and dried in vacuo overnight. The filter cake was recrystallized from dimethyl sulfoxide/10% hydrochloric acid to yield 10.5 g (75%) of product, mp 236°–237° C.

Analysis: Calculated for $C_{15}H_{10}O_2S_2$: 62.91%C; 3.52%H, Found: 62.96%C; 3.46%H.

EXAMPLE 3

5-[2-(Benzo[b]thiophen-2-yl)ethenyl]thiophene-2-(N-methyl)hydroxamic acid

To a stirred suspension of 5-[2-(benzo[b]thiophen-2-yl)ethenyl]thiophene-2-carboxylic acid (9.11 g) and dichloromethane (900 ml) was added over 5 mins thionyl chloride (7.56 g). The mixture was refluxed overnight. The solvent was removed in vacuo to give 9.25 g of 5-[2-(benzo[b]thiophen-2-yl)ethenyl]thiophene-2-carboxylic acid chloride.

To a stirred solution of the acid chloride (4.5 g), water (48 ml) and tetrahydrofuran (210 ml) was added N-methylhydroxylamine hydrochloride (4.93 g) and triethylamine (8.96 g). After stirring for 0.5 hr, the solution was poured into 2N hydrochloric acid (500 ml). The precipitate was dried in vacuo overnight, and then extracted with ethyl acetate in a Soxhlet apparatus. The extract was cooled and the precipitate was collected and dried in vacuo to give 2.68 g (57%) of product, mp 175°–177° C. (dec.).

Analysis: Calculated for $C_{16}H_{13}NO_2S_2$: 60.93%C; 4.15%H; 4.44%N, Found: 60.92%C; 4.02%H; 4.47%N.

EXAMPLE 4

5-[2-(Benzo[b]thiophen-2-yl)ethenyl]thiophene2-carboxylic acid ethyl ester

To a stirred suspension of 5-[2-(benzo[b]thiophen-2yl)ethenyl]thiophene-2-carboxylic acid (9.11 g) and dichloromethane (900 ml) was added thionyl chloride (7.56 g) over 5 mins. The mixture was refluxed overnight. The solvent was removed in vacuo to give 9.25 g of 5-[2-(benzo[b]thiophen-2-yl)ethenyl]thiophene-2-carboxylic acid chloride.

A stirred suspension of the acid chloride (4.33 g), pyridine (1.23 g) and anhydrous ethanol (500 ml) was refluxed overnight. The solution was concentrated, and the resulting solid was dissolved in ether and filtered. The filtrate was concentrated and purified by high performance liquid chromatography (silica gel, eluted with ethyl acetate). The appropriate fractions were combined and evaporated. The residue was recrystallized from hexane to yield 2.80 g (63%) of product, mp 116°–117° C.

Analysis: Calculated for $C_{17}H_{14}O_2S_2$: 64.94%C; 4.49%H, Found: 64.94%C; 4.40%H.

EXAMPLE 5

5-[2-(Benzo[b]thiophen-2-yl)ethenyl]-2-(3-bromopropyl)thiophene

To a stirred, chilled (−65° C.) solution of 2-[2-(benzo[b]thiophen-2-yl)-ethenyl]thiophene (8.1 g) and tetrahydrofuran (100 ml) was added over 15 mins phenyl lithium (18 ml of a 2.0M solution in cyclohexane). The mixture was stirred for 1 hr, and 1,3-dibromopropane (40.5 g) was added. The solution was allowed to warm to room temperature, and was refluxed overnight. The reaction mixture was quenched with methanol (30 ml) and water (100 ml). The organic phase was evaporated in vacuo, and the residue was extracted with dichloromethane. The combined, dried over anhydrous sodium sulfate organic phase was concentrated. The residue was purified by high pressure liquid chromatography (silica gel, eluted with 7:1 hexane: dichloromethane). The appropriate fractions were combined and evaporated to yield 2.15 g (18%) of product, mp 109°–111° C.

Analysis: Calculated for $C_{17}H_{15}BrS_2$: 56.20%C; 4.16%H, Found: 56.81%C; 3.96%H.

EXAMPLE 6

5-[2-(Benzo[b]thiophen-2-yl)ethenyl-2-[3-(N-hydroxy-N-methylamino)propyl]-thiophene To a stirred solution of N-hydroxylmethylamine hydrochloride (9.23 g) and tetrahydrofuran (300 ml) was added potassium-t-butoxide. The suspension was stirred 0.5 hr, and a solution of 5-[2-(benzo[b]thiophen-2-yl)ethenyl]-2-(3-bromopropyl)thiophene (6.0 g) and tetrahydrofuran (50 ml) was added. The mixture was heated at reflux overnight and was poured into water (500 ml). The organic solvent was removed in vacuo, and the resulting residue was extracted with dichloromethane. The combined organic phase was washed with water and brine, dried over anhydrous sodium sulfate, filtered, and concentrated. The residue was purified by high pressure liquid chromatography (silica gel eluted with ethyl acetate). The appropriate fractions were combined and evaporated to yield 4.44 g (81%) of product, mp 148°–149° C.

Analysis: Calculated for $C_{18}H_{19}NOS_2$: 65.62%C; 5.81%H; 4.25%N, Found: 66.00%; 5.96%H; 4.08%N.

EXAMPLE 7

3-[2-(5-Bromo-2-thienyl)ethenyl]benzo[b]thiophene

To a stirred, chilled (10° C.) suspension of hexane-washed sodium hydride (60% dispersion in mineral oil, 1.04 g) and dimethoxyethane (125 ml) was added a solution of diethyl-3-benzo[b]thienylphosphonate (10.35 g) and dimethoxyethane (40 ml) over 5 mins. The mixture was stirred 0.5 hr, and a solution of 5-bromo-2-thiophene carboxaldehyde (6.95 g) and dimethoxyethane (20 ml) was added over 10 mins. The suspension was stirred at room temperature overnight. Water (400 ml) was added, and the organic phase was removed in vacuo. The aqueous phase was extracted with dichloromethane, and the combined, dried over anhydrous sodium sulfate organic phase was evaporated. The residue was purified by high pressure liquid chromatography (silica gel, loaded in 2:1 hexane:dichloromethane, eluted with hexane). The appropriate fractions were combined and evaporated to yield 5.36 g (46%) of product, mp 71.5°–73° C.

Analysis: Calculated for $C_{14}H_9BrS_2$: 52.34%C; 2.82%H, Found: 52.42%C; 2.84%H.

EXAMPLE 8

5-[2-(Benzo[b]thiophen-3-yl)ethenyl]thiophene-2-carboxylic acid

To a stirred, chilled (−70° C.) solution of 3-[2-(5-bromo-2-thienyl)-ethenyl]benzo[b]thiophene (15.0 g) and ether (500 ml) was added n-butyl lithium (20.5 ml, 2.5M solution in hexanes) over 15 mins., under a nitrogen atmosphere. The mixture was stirred 1.5 hr, and was transferred under nitrogen to a vessel containing a large excess of dry ice and ether (500 ml). The suspension was stirred at room temperature overnight. The mixture was poured into water (1 L) and the mixture was basified with 2.5N sodium hydroxide solution. The organic phase was removed. The aqueous phase was acidified with 10% hydrochloric acid and extracted with dichloromethane. The combined, dried over anhydrous sodium sulfate, organic phase was concentrated, and the residue was recrystallized from toluene to give 7.10 g (52.8%) of product, mp 196°–197° C.

Analysis: Calculated for $C_{15}H_{10}O_2S_2$: 62.91%C; 3.52%H, Found: 62.96%C; 3.46%H.

EXAMPLE 9

5-[2-(Benzo[b]thiophen-3-yl)ethenyl]thiophene-2-carboxylic acid ether ester

To a solution of 5-[2-(benzo[b]thiophen-3-yl)ethenyl]thiophene-2-carboxylic acid (5.8 g) and dichloromethane (250 ml) was added thionyl chloride (5.3 g) over 5 mins. The mixture was refluxed overnight. The solution was cooled and evaporated to yield 6.5 g of the acid chloride. A solution of the acid chloride, pyridine (1.9 g) and absolute ethanol (500 ml) was refluxed overnight. The solvent was evaporated, and the resulting solid was dissolved in ether (100 ml) and filtered. The filtrate was evaporated. The residue was purified by high performance liquid chromatography (silica gel, eluted with ethyl acetate). The appropriate fraction was evaporated and recrystallized from isooctane to give 2.7 g (42%) of product, mp 83.5°–85° C.

Analysis: Calculated for $C_{17}H_{14}O_2S_2$: 64.94%C; 4.49%H, Found: 65.01%C; 4.45%H.

EXAMPLE 10

5-[2-(Benzo[b]thiophen-3-yl)ethenyl]thiophene-2-carboxaldehyde

To a chilled (−70° C.), stirred solution of 3-[2-(5-bromo-2-thienyl)-ethenyl]benzo[b]thiophene (16.98 g) and ether (300 ml) was added n-butyllithium (23 ml of a 2.5M solution in hexanes), under nitrogen, over 5 mins. After stirring for 1.5 hrs, the mixture was added via canula to a solution of N,N-dimethylformamide (19.3 g) and ether (500 ml). The mixture was allowed to warm to room temperature, stirred overnight, and then poured into water (500 ml). The aqueous phase was separated, and the organic phase was washed with 10% aqueous hydrochloric acid, water, and 5% aqueous sodium bicarbonate solution. The solution was dried over anhydrous sodium sulfate, filtered, and concentrated to give 14.9 g of solid. A lot of similarly prepared material (4.1 g) was combined with the solid, and the combined material was purified by high performance liquid chromatography (silica gel, loaded and eluted with 10% hexane in dichloromethane). The appropriate fractions were combined and evaporated. The residue was recrystallized from toluene/hexane to give 9.25 g (51%) of product, mp 105°–107° C.

Analysis: Calculated for $C_{15}H_{10}OS_2$: 66.64%C; 3.73%H, Found: 66.70%C; 3.74%H.

EXAMPLE 11

3-[2-(5-Hydroxymethyl-2-thienyl)ethenyl]benzo[b]thiophene

A stirred, chilled (0° C.) suspension of sodium borohydride (0.50 g) and absolute ethanol (250 ml), under nitrogen, was treated in portions with 5-[2-(benzo[b]thiophen-3-yl)ethenyl]thiophene-2-carboxaldehyde (3.0 g). After stirring at room temperature overnight, the mixture was poured into water (250 ml). The organic phase was removed in vacuo, and the resulting aqueous phase was extracted with dichloromethane. The combined, dried over anhydrous magnesium sulfate, filtered organic phase was evaporated. The residue was purified by high performance liquid chromatography (silica gel, loaded and eluted first with dichloromethane, then with ethyl acetate). The appropriate fractions were combined and evaporated. The residue was recrystallized from toluene/hexane to yield 2.15 g (71%) of product, mp 68°–70° C.

Analysis: Calculated for $C_{15}H_{12}OS$: 66.14%C; 4.44%H, Found: 66.44%C; 4.44%H.

EXAMPLE 12

3-[2-(5-Acetoxymethyl-2-thienyl)ethenyl]benzo[b]thiophene

To a stirred solution of 3-[2-(5-hydroxymethyl-2-thienyl)ethenyl]-benzo[b]thiophene (5.35 g) and pyridine (50 ml) was added over 5 mins acetyl chloride (1.54 g). The mixture was stirred at ambient temperature overnight and was poured into water (500 ml). The mixture was extracted with dichlormethane, and the combined organic phase was washed with 5% aqueous hydrochloric acid, dried over anhydrous sodium sulfate, filtered, and concentrated. The residue was purified by high performance liquid chromatography (silica gel, sample loaded in dichloromethane, eluted with 15% ethyl acetate in hexane.) The appropriate fractions were combined and concentrated. The residue was recrystallized from cyclohexane to afford 3.15 g (51%) of product, mp 66°–68° C.

Analysis: Calculated for $C_{17}H_{14}O_2S_2$: 64.94%C; 4.49%H, Found: 64.95%C; 4.44%H.

EXAMPLE 13

5-[2-Benzo[b]thiophen-3-yl)ethenyl]thiophene-2-carboxylic acid octyl ester

The acid chloride of 5-[2-(benzo[b]thiophen-3-yl)ethenyl]thiophene-2-carboxylic acid was prepared as described in Example 9. To a solution of 5-[2-(benzo[b]thiophen-3-yl)ethenyl]thiophene-2-carboxylic acid chloride (4.7 g) and pyridine (50 ml) was added octanol (2.0 g). After refluxing overnight, the mixture was poured into water (500 ml), extracted with dichloromethane, and the combined organic phase was washed with 5% hydrochloric acid and water. The dried over anhydrous sodium sulfate, filtered, organic phase was concentrated. The residue was purified by high performance liquid chromatography (silica gel column, loaded and eluted with dichloromethane). The appropriate fractions were combined and evaporated. The residue was recrystallized from hexane/dichloromethane to yield 2.20 g (36%) of product, mp 37°–40° C.

Analysis: Calculated for $C_{23}H_{26}O_2S_2$: 69.31%C; 6.57%H, Found: 69.32%C; 6.63%H.

EXAMPLE 14

5-[2-Benzo[b]thiophen-3-yl)ethenyl]thiophene-2-carboxylic acid (2,2-dimethyl-1,3-dioxolan-4-yl)hydroxymethyl ester The acid chloride of 5-[2-(benzo[b]thiophen-3-yl)ethenyl]thiophene-2-carboxylic acid was prepared as described in Example 9. To a solution of 5-[2-(benzo[b]thiophen-3-yl)ethenyl]thiophene-2-carboxylic acid chloride (5.0 g) and pyridine (50 ml) was added 2,2-dimethyl-1,3-dioxolane-4-methanol (2.17 g). After refluxing overnight, the mixture was evaporated. The residue was dissolved in ethyl acetate, filtered, and concentrated. The residue was purified by high performance liquid chromatography (silica gel, loaded and eluted in 2:1 ethyl acetate:hexane). The appropriate fractions were combined and evaporated. Trituration of the residue with hexane yielded 2.60 g (39%) of product, mp 77°–79° C.

Analysis: Calculated for $C_{21}H_{20}O_4S_4$: 62.98%C; 5.03%H, Found: 62.93%C; 5.09%H.

EXAMPLE 15

3-[2-(5-Methyl-2-thienyl)ethenyl]benzo[b]thiophene

To a chilled (−70° C.), stirred solution of 3-[2-(5-bromo-2-thienyl)ethenyl]-benzo[b]thiophene (5.00 g) and ether (250 ml) was added n-butyllithium (6.8 ml of a 2.5M solution in hexanes), under nitrogen, over 2 mins. The mixture was stirred and chilled for 1.5 hrs. Methyl iodide (8.83 g) was added, and the mixture was allowed to warm to ambient temperature, with stirring, overnight. Water (200 ml) was added. The mixture was agitated, and the organic phase was separated. The organic phase was washed with water, dried over anhydrous sodium sulfate, filtered, and concentrated. The residue was purified by high performance liquid chromatography (silica gel, eluted with 10% dichloromethane in hexane). The appropriate fractions were combined and evaporated to yield 3.53 g (88%) of product, mp 62°–64° C.

Analysis: Calculated for $C_{15}H_{12}S_2$: 70.27%C; 4.72%H, Found: 70.05%C; 4.69%H.

EXAMPLE 16

5-[2-(Benzo[b]thiophen-3-yl)ethenyl]thiophene-2-carboxylic acid 3-hydroxymethylpyridyl ester The acid chloride of 5-[2-(benzo[b]thiophen-3-yl)ethenyl]thiophene-2-carboxylic acid was prepared as described in Example 9. To a suspension of 5-[2-(benzo[b]thiophen-3-yl)ethenyl]thiophene2-carboxylic acid chloride (5.00 g) and pyridine (50 ml) was added 3-pyridylcarbinol (1.79 g). After refluxing overnight, the mixture was evaporated, and the residue was dissolved in ether, filtered, and concentrated. The residue was purified by high performance liquid chromatography (silica gel, eluted with 2:1 ethyl acetate:hexane). The appropriate fractions were combined and evaporated. The residue was recrystallized from toluene/hexane to afford 1.4 g (23%) of the product, mp 97°–98° C.

Analysis: Calculated for $C_{21}H_{15}NO_2S_2$: 66.82%C; 4.01%H; 3.71%N, Found: 66.75%C; 4.04%H; 3.70%N.

EXAMPLE 17

3-[5-[2-(Benzo[b]thiophen-3-yl)ethenyl]thiophen-2-yl]-2-propenoic acid ethyl ester To a chilled (10° C.), stirred solution of triethyl phosphonacetate (9.3 g) and dimethoxyethane (100 ml) was added potassium hexamethyldisilazane (63 ml of a 0.66M solution in toluene). The solution was stirred at ambient temperature for ½ hr, and a solution of 5-[2-(benzo[b]thiopen-3-yl)ethenyl]thiophene-2-carboxaldehyde (11.2 g) and dimethoxyethane (90 ml) was added over 5 mins. The mixture was stirred overnight and quenched with water (5 ml) and 10% hydrochloric acid (100 ml). The organic phase was evaporated, and the residue was extracted with dichloromethane. The combined organic phase was washed with 5% hydrochloric acid, water and brine, dried over anhydrous sodium sulfate, filtered, and concentrated. A 5-g sample of the residue was recrystallized from hexane to afford 3.4 g (68%) of product, mp 99°–100°C.

Analysis: Calculated for $C_{19}H_{16}O_2S_2$:67.03%C; 4.74%H, Found: 66.94%C; 4.67%H.

EXAMPLE 18

5-[2-(Benzo[b]thiophen-3-yl)ethenyl]thiophene-2-(N-methyl)hydroxamic acid

To a stirred suspension of 5-[2-(benzo[b]thiophen-3-yl)ethenyl]thiophene-2-carboxylic acid (8.9 g) and dichloromethane (250 ml) was added thionyl chloride (7.38 g) over 5 mins. The mixture was refluxed overnight. The solvent was removed in vacuo to yield 8.5 g of 5-[2-(benzo[b]thiophen-3-yl)ethenyl]thiophene-2-carboxylic acid chloride. To a stirred solution of the acid chloride (8.5 g), water (80 ml), and tetrahydrofuran (420 ml) was added N-methylhydroxylamine hydrochloride (9.32 g) and triethylamine (16.9 g). After stirring overnight, the solution was poured into 600 ml of 2N hydrochloric acid. The suspension was extracted with dichloromethane, and the combined organic phase was washed with water and brine. The solution was dried over anhydrous sodium sulfate, filtered, and concentrated. The residue was purified by high performance liquid chromatography, (silica gel, eluted with 5:3 ethyl acetate:hexane). The appropriate fractions were combined and evaporated. Recrystallization of the residue from toluene afforded 2.60 g (30%) of product, mp 157°–159° C.

Analysis: Calculated for $C_{16}H_{13}NO_2S_2$: 60.93%C; 4.15%H; 4.44%N, Found: 61.10%C, 4.14%H; 4.45%N.

EXAMPLE 19

5-[2-(Benzo[b]thiophen-3-yl)ethenyl]thiophene-2-carboxylic acid 2,3-dihydroxypropyl ester A stirred solution of 5-[2-benzo[b]thiophen-3-yl)ethenyl]thiophene-2-carboxylic acid (2,2-dimethyl-1,3-dioxolan-4-yl)hydroxymethyl ester (4.68 g), boric acid (7.22 g), and triethylborate (70 ml) was heated at 100° C. for 5 hrs. The solution was evaporated in vacuo at 100° C., and the residue was partitioned between ether and water. The aqueous phase was extracted with ether, and the combined organic phase was washed with water, dried over anhydrous sodium sulfate, filtered, and concentrated. The residue was purified by high performance liquid chromatography (silica gel, ethyl acetate). The appropriate fractions were combined and evaporated to yield 3.00 g (71%) of product, mp 102°–104° C.

Analysis: Calculated for $C_{18}H_{16}O_4S_2$: 59.98%C; 4.47%H, Found: 59.77%C; 4.48%H.

EXAMPLE 20

3-[5-[2-(Benzo[b]thiophen-3-yl)ethenyl]thiophen-2-yl]-2-propenoic acid

A stirred mixture of 3-[5-[2-(benzo[b]thiophen-3-yl)ethenyl]thiophen-2-yl]-2-propenoic acid ethyl ester (5.47 g), 1N aqueous potassium hydroxide solution (50 ml) and tetrahydrofuran (60 ml) was heated at reflux overnight. The mixture was concentrated in vacuo, and the residue was acidified with 10% hydrochloric acid. The mixture was extracted with dichloromethane and ethyl acetate. The combined organic phase was dried over anhydrous sodium sulfate, filtered, and concentrated. The residue was extracted (Soxhlet) overnight with ethyl acetate. The extract was reduced to a volume of 100 ml and cooled to give 2.2 g (44%) of product, mp 197°–198° C. (dec.).

Analysis:
Calculated for $C_{17}H_{12}O_2S_2$: 65.36%C; 3.87%H,
Found: 65.26%C; 3.88%H.

EXAMPLE 21

Ethyl 2-acetamido-3-[5-[2-(benzo[b]thiophen-3-yl)ethenyl]thiophen-2-yl]-3-hydroxypropionate A solution of 5-[2-(benzo[b]thiophen-3-yl)ethenyl]-thiophene-2-carboxaldehyde (12.0 g), N-acetamidomonoethyl malonate (8.4 g) triethylamine (4.5 g), and tetrahydrofuran (200 ml) was stirred at ambient temperature for 6 days. The solvent was evaporated, and the residue was purified by high performance liquid chromatography (silica gel, sample loaded in dichloromethane, eluted with 20% hexane/ethyl acetate). The appropriate fractions were combined and evaporated to yield 5.2 g (29%) of product, mp 157°–159° C.

Analysis: Calculated for $C_{21}H_{21}NO_4S_2$: 60.70%C; 5.09%H; 3.37%N, Found: 60.33%C; 5.15%H; 3.40%N.

EXAMPLE 22

N-[[5-[2-(Benzo[b]thiophen-3-yl)ethenyl]thiophen-2-yl]-1,3-dihydroxy-2-propanyl]acetamide A stirred, chilled (−5° C.) suspension of ethyl 2-acetamido-3-[5-[2-(benzo[b]-thiophen-3-yl)ethenyl]thiophen-2-yl]-3-hydroxypropionate (4.0 g) and tetrahydrofuran (40 ml) was treated with lithium borohydride (5.8 ml of a 2.0M solution in tetrahydrofuran) over 3 mins. After stirring overnight at ambient temperature, the mixture was sequentially quenched with methanol (5 ml), water (20 ml), and 10% hydrochloric acid (5 ml). The organic solvent was removed in vacuo, and the aqueous phase was basified with 10% sodium hydroxide solution and extracted with dichloromethane and ether. The combined dried over anhydrous sodium sulfate organic phase was filtered and evaporated. The residue was purified by high performance liquid chromatography (silica gel, sample loaded in dichloromethane, eluted with 10% methanol in dichloromethane). The appropriate fractions were combined and evaporated to yield 2.23 g (62%) of product, mp 144°–145° C.

Analysis: Calculated for $C_{19}H_{19}NO_3S_2$: 61.10%C; 5.13%H; 3.75%N, Found: 60.76%C; 5.08%H; 3.72%N.

EXAMPLE 23

5-[2-(Benzo[b]thiophen-3-yl)ethenyl]thiophene-2-(2-amino-3-hydroxy-3-propanol)

A stirred solution of N-[[5-[2-(benzo[b]thiophen-3-yl)ethenyl]thiophen-2-yl]-1,3-dihydroxy-2-propanyl]acetamide (4.53 g), potassium hydroxide (2.04 g), and 2-propanol (150 ml) was heated at reflux overnight. The mixture was diluted with 200 ml of water, and the 2-propanol was evaporated. The residue was diluted with 200 ml of brine and was extracted with ethyl acetate. The combined, dried over anhydrous sodium sulfate organic phase was evaporated. The residue was purified by high performance liquid chromatography (silica gel, sample loaded and eluted with methanol). The appropriate fractions were combined and evaporated. The residue was dissolved in ethyl acetate, filtered, and evaporated. The residue was dissolved in absolute ethanol, and the solution was evaporated to give 2.7 g (67%) of product, mp 106°–108° C.

Analysis: Calculated for $C_{17}H_{17}NO_2S_2$: 61.60%C; 5.17%H; 4.23%N, Found: 61.45%C; 5.13%H; 4.15%N.

EXAMPLE 24

3-[2-(2-Hydroxymethyl-3-thienyl)ethenyl]benzo[b]thiophene

To a stirred, chilled, (−70° C.) solution of 3-bromo-2-hydroxymethylthiophene (19.0 g) and tetrahydrofuran (250 ml) was added n-butyllithium (88 ml of a 2.5M solution in hexanes), under nitrogen, over 45 mins. The solution was stirred and chilled for 1 hr and was transferred via canula to a vessel containing a solution of N,N-dimethylformamide (7.9 g) and tetrahydrofuran (250 ml). The mixture was allowed to warm to ambient temperature overnight, with stirring. Methanol (20 ml) and water (200 ml) were added. The organic phase was removed in vacuo, and the residue was extracted with dichloromethane. The combined organic phase was washed with 5% sodium bicarbonate solution and brine, dried over anhydrous magnesium sulfate, filtered, and concentrated. The residue was purified by high performance liquid chromatography (silica gel, eluted with 40% ethyl acetate in hexane). The appropriate fractions were combined and evaporated to afford 3.5 g (35%) of 2-hydroxymethyl-3-thiophenecarboxaldehyde.

To a stirred, chilled (10° C.) solution of potassium hexamethyldisilazane (29 ml of a 0.66M solution in toluene) and dimethoxyethane (50 ml) was added a solution of 3-benzo[b]thienylphosphonate (5.5 g) and dimethyoxyethane (10 ml) over 10 mins. The solution was allowed to warm to ambient temperature and was stirred 1.5 hrs. A solution of 2-hydroxymethyl-3-thiophenecarboxaldehyde (2.75 g) and dimethoxyethane (5 ml) was added. After stirring overnight the mixture was quenched with 5 ml of water and with 50 ml of 10% hydrochloric acid. The organic phase was extracted with dichloromethane. The combined, dried over anhydrous sodium sulfate organic phase was concentrated. The residue was purified by high performance liquid chromatography (silica gel, loaded and eluted with dichloromethane). The appropriate fractions were combined and evaporated to give 1.4 g (24%) of product, mp 114°–115° C.

Analysis: Calculated for $C_{15}H_{12}OS_2$: 66.14%C; 4.44%H, Found: 66.04%C; 4.38%H.

REACTION SCHEME A

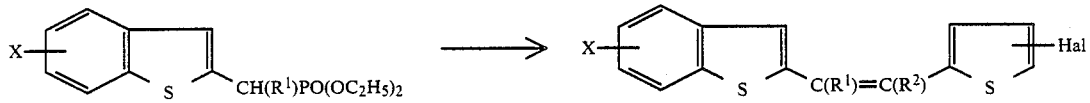

-continued
REACTION SCHEME A
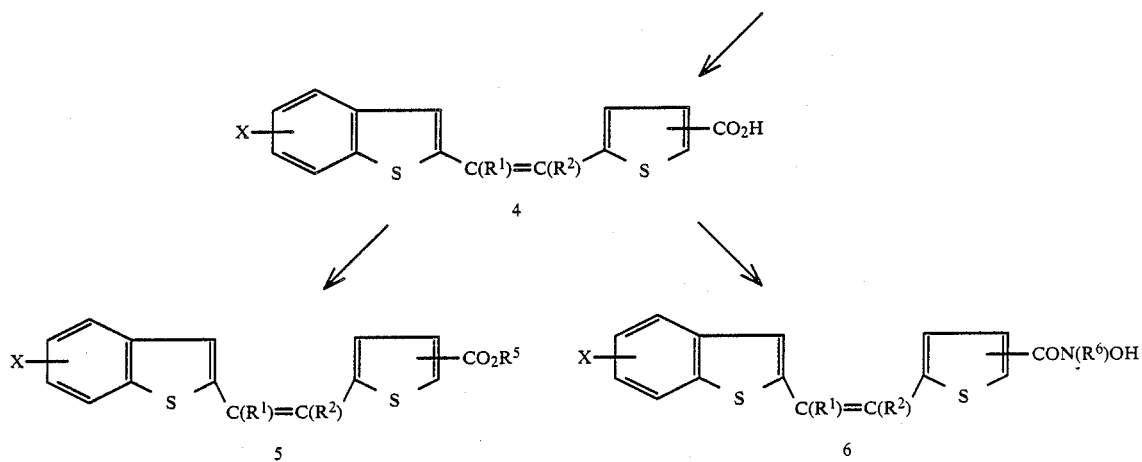
Wherein $R^1$, $R^2$, $R^5$, $R^6$, X, and Hal are as hereinbefore described
REACTION SCHEME B
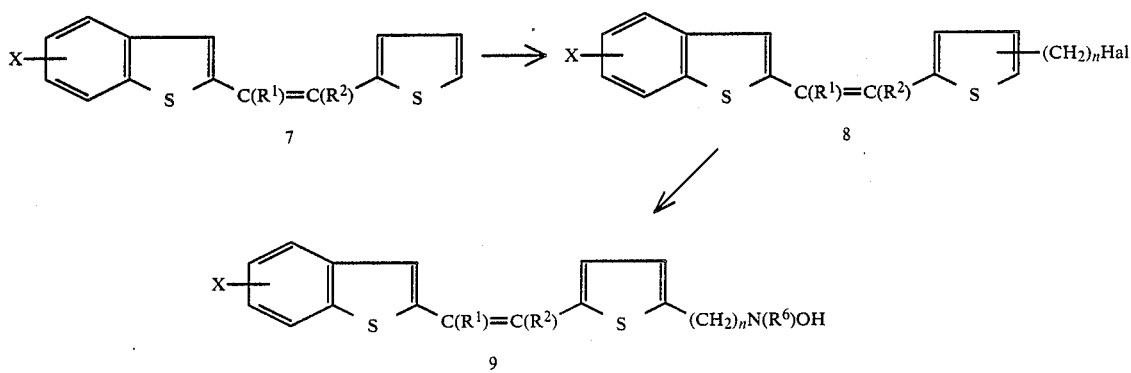
Wherein $R^1$, $R^2$, $R^6$, X, Hal and n are as hereinbefore described
REACTION SCHEME C
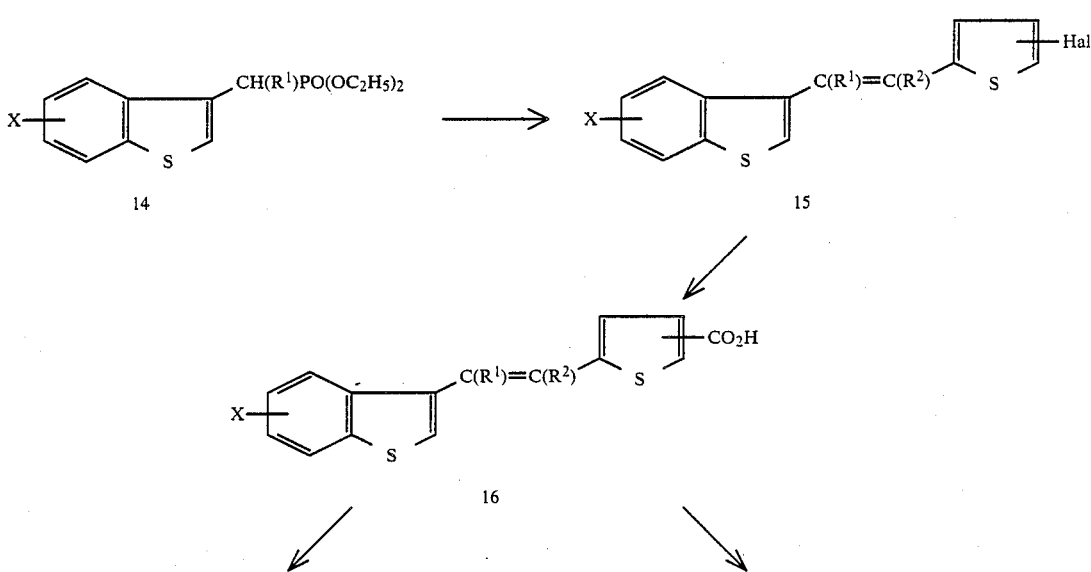

-continued
REACTION SCHEME C
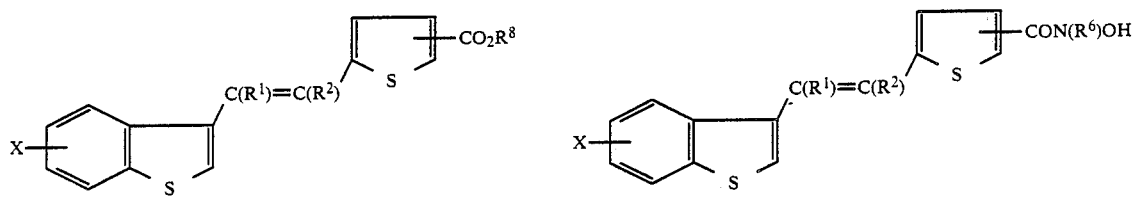
Wherein $R^1, R^2, R^6, R^8$, and X are as hereinbefore described
REACTION SCHEME D
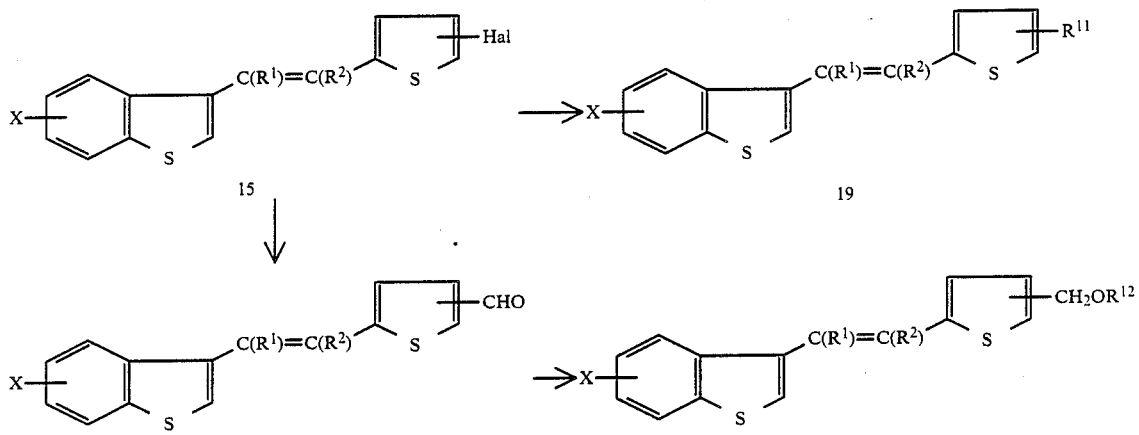
Wherein $R^1, R^2, R^{11}, R^{12}$, X, and Hal are as hereinbefore described

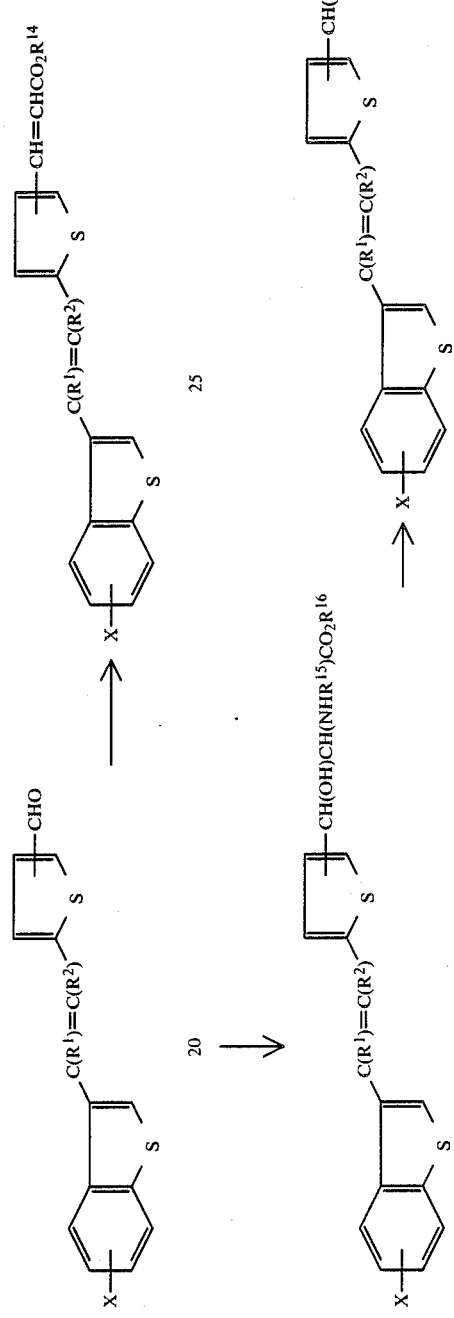
REACTION SCHEME E
Wherein $R^1$, $R^2$, $R^{14}$, $R^{15}$, $R^{16}$, and X are as hereinbefore described

REACTION SCHEME F

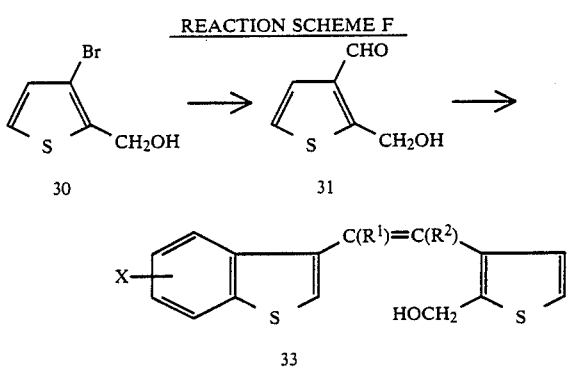

Wherein R¹, R², and X are as hereinbefore described

We claim:
1. A compound of the formula

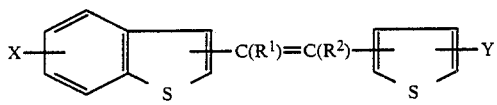

wherein R¹ and R² are independently hydrogen or loweralkyl; X is hydrogen, loweralkyl, loweralkoxy, halogen, or trifluoromethyl; Y is halogen, loweralkyl, hydroxymethyl, formyl, carboxy, loweralkoxycarbonyl, loweralkanoyloxymethyl, (N-loweralkyl-N-hydroxyamino)carbonyl, ω-haloloweralkyl, carboxyloweralkylidene, loweralkoxycarbonylloweralkylidene, (N-loweralkyl-N-hydroxyamino)loweralkyl, (N-cycloalkyl-N-hydroxyamino)carbonyl, (N-cycloalkyl-N-hydroxamino)loweralkyl, a group of the formula

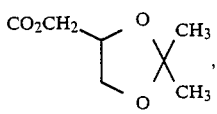

a group of the formula

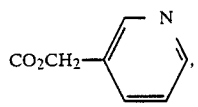

a group of the formula $CO_2CH_2CH(OH)CH_2OH$, a group of the formula $CH(OH)CH(CO_2R^3)NHCOR^4$ wherein $R^3$ and $R^4$ are loweralkyl, a group of the formula $CH(OH)CH(CH_2OH)NHCOR^4$ where in $R^4$ is loweralkyl, or a group of the formula $CH(OH)CH(CH_2OH)NH_2$; a geometric or optical isomer thereof, or the pharmaceutically acceptable salt thereof.

2. A compound according to claim 1 wherein R¹ and R² are hydrogen; X is hydrogen; and Y is hydroxymethyl, carboxyloweralkylidene or (N-loweralkyl-N-hydroxyamino)carboxyl or (N-cycloalkyl-N-hydroxyamino)carbonyl.

3. The compound according to claim 1 which is 2-[2-(5-bromo-2-thienyl]benzo[b]thiophene.

4. The compound according to claim 1 which is 5-[2-(benzo[b]thiophen-2-yl)ethenyl]thiophene-2-carboxylic acid.

5. The compound according to claim 2 which is 5-[2-(benzo[b]thiophen-2-yl)ethenyl]thiophene-2-(N-methyl)hydroxamic acid.

6. The compound according to claim 1 which is 5-[2-(benzo[b]thiophen-2-yl)ethenyl]thiophene-2-carboxylic acid ethyl ester.

7. The compound according to claim 1 which is 5-[2-(benzo[b]thiophen2-yl)ethenyl]-2-(3-bromopropyl)thiophene.

8. The compound according to claim 1 which is 5-[2-(benzo[b]thiophen-2-yl)ethenyl]-2-[3-(N-hydroxy-N-methylamino)propyl]thiophene.

9. The compound according to claim 1 which is 3-[2-(5-bromo-2-thienyl)ethenyl]benzo[b]thiophene.

10. The compound according to claim 1 which is 5-[2-(benzo[b]thiophen-3-yl)ethenyl]thiophene-2-carboxylic acid.

11. The compound according to claim 1 which is 5-[2-(benzo[b]thiophen-3-yl)ethenyl]thiophene-2-carboxylic acid ethyl ester.

12. The compound according to claim 1 which is 5-[2-(benzo[b]thiophen-3-yl)ethenyl]thiophene-2-carboxaldehyde.

13. The compound according to claim 1 which is 3-[2-(5-hydroxymethyl-2-thienyl)ethenyl]benzo[b]thiophene.

14. The compound according to claim 1 which is 3-[2-(5-acetoxymethyl-2-thienyl)ethenyl]benzo[b]thiophene.

15. The compound according to claim 1 which is 5-[2-(benzo[b]thiophen-3-yl)ethenyl]thiophene-2-carboxylic acid octyl ester.

16. The compound according to claim 1 which is 5-[2-(benzo[b]thiophen-3-yl)ethenyl]thiophene-2-carboxylic acid (2,2-dimethyl-1,3-dioxolan-4-yl)hydroxymethyl ester.

17. The compound according to claim 1 which is 3-[2-(5-methyl-2-thienyl)ethenyl]benzo[b]thiophene.

18. The compound according to claim 1 which is 5-[2-(benzo[b]thiophen-3-yl)ethenyl]thiophene-2-carboxylic acid 3-hydroxymethylpyridyl ester.

19. The compound according to claim 2 which is 3-[5-[2-benzo[b]thiophen-3-yl)ethenyl]thiophen-2-yl]-2-propenoic acid ethyl ester.

20. The compound according to claim 2 which is 5-[2-(benzo[b]thiophen-3-yl)ethenyl]thiophene-2-(N-methyl)hydroxamic acid.

21. The compound according to claim 1 which is 5-[2-(benzo[b]thiophen-3-yl)ethenyl]thiophene-2-carboxylic acid 2,3-dihydroxypropyl ester.

22. The compound according to claim 2 which is 3-[5-[2-(benzo[b]thiophen-3-yl)ethenyl]thiophen-2-yl]-2-propenoic acid.

23. The compound according to claim 1 which is ethyl 2-acetamido-3-[5-[2-(benzo[b]thiophen-3-yl)ethenyl]-thiophen-2-yl]-3-hydroxypropionate.

24. The compound according to claim 1 which is N-[[5-[2-(benzo[b]thiophen-3-yl)ethenyl]thiophen-2-yl]-1,3-dihydroxy-2-propanyl]acetamide.

25. The compound according to claim 1 which is 5-[2-(benzo[b]thiophen-3-yl)ethenyl]thiophene-2-(2-amino-3-hydroxy)-3-propanol.

26. The compound according to claim 2 which is 3-[2-(2-hydroxymethyl-3-thienyl)ethenyl]benzo[b]thiophene.

27. A method of reducing inflammation in mammals comprising administering topically to a mammal requiring inflammation reduction a topical inflammation reducing effective amount of a compound or a pharmaceutically acceptable salt thereof according to claim 1.

28. A topical inflammation reducing composition comprising an inert inflammation reducing adjuvant and as the active ingredient a topical inflammation reducing effective amount of a compound or a pharmaceutically acceptable salt thereof according to claim 1.

* * * * *